United States Patent [19]
Van Nispen et al.

[11] Patent Number: 5,719,128
[45] Date of Patent: Feb. 17, 1998

[54] FACTOR IIA INHIBITORS

[75] Inventors: Johannes Wilhelmus Franciscus Maria Van Nispen, Oss; Henricus Carl Joseph Ottenheym, Milsbeek; Jacobus Albertus Maria Peters; Arie Visser, both of Oss; Wilhelmientje Jetten, Culemborg, all of Netherlands

[73] Assignee: Akzo Nobel N.V., Arnhem, Netherlands

[21] Appl. No.: 458,997

[22] PCT Filed: Feb. 4, 1992

[86] PCT No.: PCT/EP92/00273

§ 371 Date: Sep. 16, 1993

§ 102(e) Date: Sep. 16, 1993

[87] PCT Pub. No.: WO92/13877

PCT Pub. Date: Aug. 20, 1992

Related U.S. Application Data

[63] Continuation of Ser. No. 98,281, Sep. 16, 1993, abandoned.

[30] Foreign Application Priority Data

Feb. 4, 1991 [EP] European Pat. Off. .............. 91200201

[51] Int. Cl.$^6$ .............. C07K 7/02; C07K 7/04; A61K 38/00; A61K 38/08

[52] U.S. Cl. .............. 514/17; 514/16; 514/18; 530/329; 530/330

[58] Field of Search .............. 530/329, 330; 514/16, 17, 18

[56] References Cited

U.S. PATENT DOCUMENTS 4,318,904  3/1982  Shaw et al. .............. 424/177

FOREIGN PATENT DOCUMENTS 1 118280  9/1984  European Pat. Off. .

OTHER PUBLICATIONS

J.M. Maraganore, "Design and Characterization of Hirulogs: A Novel Class of Bivalent Peptide Inhibitors of Thrombin," *Biochemistry*, vol. 29, No. 30, pp.7095–7101, Jul. 1990, Easton, PA, USA.

K. Krupinski, "Antithrombotic Effects of Three Inhibitors in a Rat Model of Laser–Induced Thrombosis," *Haemostasis*, vol. 19, No. 2, pp. 74–82, 1989.

T. Kline, "Hirulog Peptides with Scissle Bond Replacements Resistant to Thrombin Cleavage," *Biocheical and Biophysical Research Communications*, vol. 177, No. 3, pp. 1049–1055, Jun. 28, 1991, USA.

*Primary Examiner*—Cecilia J. Tsang
*Assistant Examiner*—Michael Borin
*Attorney, Agent, or Firm*—Mary E. Gormley

[57] ABSTRACT

Disclosed are compounds of the formula: X Y Z A P Q T which are highly potent, selective factor IIa inhibitors, X, when present, may be connected to T, may be H, $CH_3$, an acyl group, or a general protective group. Y is D-DPA, D-Phe, D-Val, D-Ile, D-Nle, a phenylsulfonyl, Dansyle, or 8-(1,2,3,4-tetrahydroquinolinosulfonyl) compound. Z, when present, is Gly, L/D-Pro, L/D-Ala, L/D-Leu, aminoisobutyric acid, a substituted or unsubstituted L/D-Pro ring homologue, or L/D-Val. A may be (I) wherein M is —CO—$CF_2$—(CO)$_s$—, —(CO)$_d$—NH—, —(CO)$_d$—(CH$_2$)$_p$—, or —CH(OH)—(CH$_2$)$_p$—, d is 0–2, p and q are 0–5, and s is 0 or 1, or A is a proline-like group. P and Q (if Q is present) are substituted or unsubstituted amino acids selected from the group consisting of L/D-Phe, L/D-Cha, L/D-Nal(1), L/D-Nal(2), L/D-phenylglycinyl, L/D-Leu, L/D-Ile, L/D-Nle, L/D-Arg, L/D-Lys, or L/D-His. T may be connected to X, or may be —OH, —OR$^4$, —NH$_2$, —NHR$^4$, or —NR$^4$R$^5$, wherein R$^4$ and R$^5$ are independently selected form alkyl, aryl, (ar)alkyl, and wherein R$^4$ and R$^5$ can be cyclically bonded one to another.

6 Claims, No Drawings

FACTOR IIA INHIBITORS

This is a continuation of application U.S. Ser. No. 08/098,281, filed Sep. 16, 1993, now abandoned, which is the National Phase of PCT/EP92/00273, filed Feb. 4, 1992.

TECHNICAL FIELD

This invention relates to certain medicinal compounds and their use as anti-factor IIa inhibitors.

BACKGROUND ART

Attempts have been made in the past to make efficacious anticoagulants. One type of anticoagulant acts to prevent the production of fibrin by somehow preventing the production of an enzyme called thrombin ("factor IIa"). This is done since thrombin acts to catalyze the cleavage of fibrinogen to form fibrin, the material from which blood clots are formed.

For example, U.S. Pat. No. 4,857,508 describes certain "RGD" peptide derivatives which assertedly inhibit platelet aggregation. These peptide derivatives are believed to act by antagonizing interactions between fibrinogen and/or extracellular matrix proteins and the platelet gpIIb/IIIa receptor.

A class of bivalent peptide inhibitors of thrombin is described in Biochemistry 29, 7095-7101, 1990. These peptides, called "hirulogs", contain the active site inhibitory sequence H-D-Phe-Pro-Arg-Pro- which is linked at the C-terminus, via a spacer of a variable number of glycyl residues, to a dodecapeptide derived from hirudin, a natural thrombin inhibitor. The dodecapeptide sequence is capable of binding to the anion-binding exosite of thrombin.

U.S. Pat. Nos. 4,638,047 and 4,772,686 to Szelke et al describe certain peptides (modified partial sequences of human fibrinogen) wherein an amide bond, especially the one that corresponds to the scissile $Arg^{16}$—$Gly^{17}$ of fibrinogen, is replaced by a nonhydrolyzable isosteric linkage. These compounds are assertedly useful as thrombin inhibitors, and have the formula:

X Y Z A Pro Arg B W wherein Pro-Arg corresponds to the 18 and 19 positions of fibrinogen, X and W could be hydrogen, Y could be D-Phe, Z could be L-Pro, A could be a keto dipeptide, and have a high binding activity for thrombin.

SUMMARY OF THE INVENTION

Surprisingly it has been found that by making certain modifications to the "Pro-Arg" portion of the prior art compounds, reversible, highly potent, highly selective factor IIa inhibitors useful in inhibiting the production of fibrin are produced.

The invention thus includes compounds of the formula:

X Y Z A P Q T or a pharmaceutically acceptable salt thereof.

In this compound, X may be hydrogen, $CH_3$, an acyl group, or a general protective group (e.g. Boc, Z, or derivatives thereof).

Y is D-Phe, D-diphenylalanyl, D-Val, D-Ile, or D-Nle.

Z may be L-Ala, L-Val, L-Leu or L-Pro.

A may be

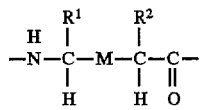

wherein M is —$(CO)_d$—NH—, —CO—$CH_2$— or —$COCF_2$—, d is 1 or 2. $R^1$ is an amino acid side chain that is characteristic of a hydrophobic, basic amino acid with an aliphatic or aromatic chain or spacer. $R^2$ may be hydrogen, methyl, or hydroxymethylene.

P is a substituted or unsubstituted amino acid selected from the group consisting of L/D-Phe (e.g. including p-chlorophenylalanyl ("pClPhe"), homo-Phe ("HPhe") and L/D-Tyr), L/D-cyclohexylalanyl, L/D-naphthylalanyl (1), L/D-naphthylalanyl (2), L/D-αMePhe, L/D-phenylglycyl, L/D-αMeTyr, L/D-Leu, L/D-Ile, L/D-Nle, L/D-Arg, L/D-Lys or L/D-His.

Q, when present, is selected from the group consisting of L/D-Arg, L/D-Lys, pipecolic acid (Pec), L/D-Nle and L/D-Tyr.

T may be —OH, —$OR^4$, —$NR^4R^5$ or —$N(CH_2)_{1-6}NR^4R^5$, wherein $R^4$ and $R^5$ are independently selected from hydrogen, alkyl, aryl, and aralkyl, or wherein $R^4$ and $R^5$ together with the nitrogen atom to which they are bonded may form a ring.

Due to their anti-factor IIa activity, these compounds have use in the manufacture of anticoagulant medicaments, especially ones intended for acute or initial administration. Once manufactured, the medicaments may be used in the treatment of mammals, including man. The medicaments are administered, on a regular basis, for example continually, to a mammal, believed to be suffering from a disease state susceptible to treatment by such medicaments. Such disease states include pulmonary embolism, thrombophlebitis, and arterial occlusion from thrombosis or embolism.

These compounds may also be used prophylactically to prevent further embolism, to forestall arterial and venous thrombosis, to prevent thromboemboli, and to prophylax against postoperative venous thrombosis or embolism.

The invention also includes a pharmaceutical composition further comprising a pharmaceutical carrier.

The invention further includes a process for preparing a compound of the formula, the process including coupling suitably protected amino acids or amino acid analogs, followed by removing the protecting groups.

DESCRIPTION OF PREFERRED EMBODIMENTS

In various preferred embodiments of the invention, X is H, a general protective group (e.g. tertiary butyloxycarbonyl, or other protecting group).

Y is preferably D-phenylalanyl.

Z is preferably L-prolyl.

A may be:

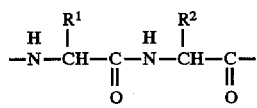

wherein $R^1$ goes to form L-Arg, but not D-Arg.

$R^1$ is

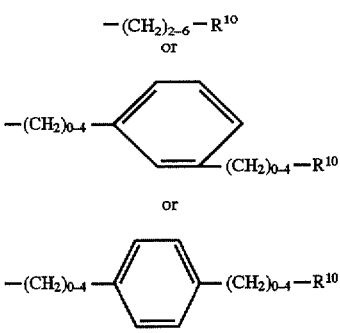

wherein $R^{10}$ is —$NH_2$, or amidino:

or guanidino:

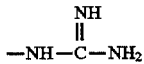

or $R^1$ is

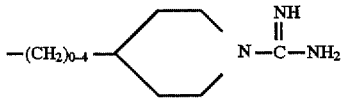

A is preferably the keto isostere:

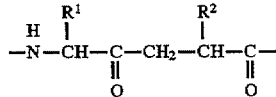

A may also be the diketo isostere:

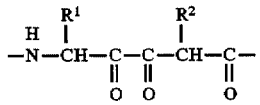

or the keto-difluoro-methylene isostere:

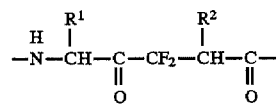

A is preferably, however, the keto isostere.

P may be as is previously defined, but preferably is L-phenylalanyl.

Q is preferably L/D-Lys or L/D-Arg.

T is preferably —OH, —$OR^4$ (wherein $R^4$ is aryl, alkyl, or aralkyl), or $NR^4R^5$ (wherein $R^5$ is alkyl, preferably methyl, ethyl or isopropyl).

In one of the most preferred embodiments of the invention, X is hydrogen, Y is D-Phe, Z is L-Pro, A is:

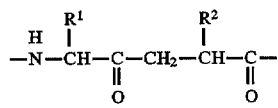

wherein $R^1$ is

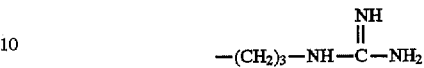

As used herein the term "pharmaceutically acceptable salt" refers to salts that retain the desired biological activity of the parent compound and preferably do not impart any undesired toxic effects. Examples of such salts are acid addition salts formed with inorganic acids, for example hydrochloric acid, hydrobromic acid, sulfuric acid, phosphoric acid nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like, or with an organic cation formed from N,N'-dibenzylethylenediamine or ethylenediamine, or combinations thereof (e.g. a zinc tannate salt).

Alkyl, as used herein, is preferably a saturated branched or unbranched hydrocarbon having one to six carbon atoms, e.g. methyl, ethyl, isopentyl, and allyl.

Aryl, as used herein, is an aromatic hydrocarbon group, preferably having 6 to 10 carbon atoms, such as phenyl or napthyl.

(Ar)alkyl, as used herein, is an arene group (having both aliphatic and aromatic portions), preferably having 7 to 13 carbon atoms, such as benzyl, ethylbenzyl, n-propylbenzyl, isobutylbenzyl.

A "substitution" with regard to the various amino acids (e.g. L/D-Phe, L/D-Cha, L/D-Nal(1), L/D-Nal(2), and L/D-phenylglycyl) generally relate to substituting a group such as alkoxy, halogen, hydroxy, nitro, or lower alkyl onto an aromatic ring for a hydrogen that would usually be present. Substitutions can also be made on the alkyl chain connecting the aromatic portion to the peptide backbone, with, for instance lower alkyl groups substituting for a hydrogen. Still further substitutions can be made at the alpha position of an amino acid, also using an alkyl group.

Substitutions with regard to the amino acid phenylalanine include compounds such as L/D-homophenylalanyl, N methyl phenylalanyl, α-methylphenylalanyl, and αmethyl-tryosyl.

Preferred substitutions involve the use of fluorine or chlorine as a halogen, and methoxy as an alkoxy group. With regard to alkyl and lower alkyl, generally alkyl groups having fewer (1 to 3) carbon atoms are preferred.

The compounds according to the general formula may be prepared in a manner conventional for such compounds. To that end, suitably $N^\alpha$ protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tert.-butyloxycarbonyl group (Boc), benzyloxycarbonyl(Z) group and substituted analogs or the base-labile 9-fluorenyl-methyloxycarbonyl (Fmoc) group.

The Z group can also be removed by catalytic hydrogenation. Other suitable protecting groups include the Nps, Bmv, Bpoc, Aloc, Msc, etc. A good overview of amino protecting groups is given in *The Peptides, Analysis, Synthesis, Biology*, Vol. 3 E. Gross and J. Meienhofer, eds., (Academic Press, New York, 1981). Protection of carboxyl groups can take place by ester formation e.g. base-labile esters like methyl or ethyl, acid labile esters like tert. butyl or hydrogenolytically labile benzyl esters. Protection of side-chain functions like those of lysine and glutamic or aspartic acid can take place using the aforementioned groups. Protection of thiol, and although not always required, of guanidino, alcohol and imidazole groups can take place using a variety of reagents such as those described in *The Peptides, Analysis, Synthesis, Biology* id. or in *Pure and Applied Chemistry*, 59(3), 331–334 (1987). Activation of the carboxyl group of the suitably protected amino acids or peptides can take place by the azide, mixed anhydride, active ester, or carbodiimide method especially with the addition of catalytic and racemization-suppressing compounds like 1-hydroxybenzotriazole, N-hydroxysuccinimide, 3-hydroxy-4-oxo-3,4-dihydro-1,2,3,-benzotriazine, N-hydroxy-5-norbornene-2,3-dicarboximide. Also the anhydrides of phosphorus based acids can be used. See, e.g. *The Peptides, Analysis, Synthesis, Biology*, supra and *Pure and Applied Chem.*, 59(3), 331–334 (1987).

It is also possible to prepare the compounds by the solid phase method of Merrifield. Different solid supports and different strategies are known. See, e.g. Barany and Merrifield in *The Peptides, Analysis, Synthesis, Biology*, Vol. 2, E. Gross and J. Meienhofer, eds., (Acad. Press, N.Y., 1980), Kneib-Cordonier and Mullen *Int. J. Peptide Protein Res.*, 30, 705–739 (1987) and Fields and Noble *Int. J. Peptide Protein Res.*, 35, 161–214 (1990). The synthesis of compounds in which a peptide bond is replaced by an isostere, can, in general, be performed using the previously described protecting groups and activation procedures. Procedures to synthesize the modified isosteres are described in the literature e.g. for the —CH$_2$—NH— isostere and for the —CO—CH$_2$— isostere.

Removal of the protecting groups, and, in the case of solid phase peptide synthesis, the cleavage from the solid support, can take place in different ways, depending on the nature of those protecting groups and the type of linker to the solid support. Usually deprotection takes place under acidic conditions and in the presence of scavengers. See, e.g. volumes 3, 5 and 9 of the series on *The Peptides, Analysis, Synthesis, Biology*, supra.

Another possibility is the application of enzymes in synthesis of such compounds; for reviews see e.g. H. D. Jakubke in *The Peptides, Analysis, Synthesis, Biology*, Vol. 9, S. Udenfriend and J. Meienhofer, eds., (Acad. Press, N.Y., 1987).

However made, the compounds are useful for the manufacture of medicaments which have use in treating disease states involving undesired blood coagulation. In such a case the particular compound synthesized will typically be associated with a pharmaceutical carrier. Pharmaceutical carriers vary from things as relatively simple as sterilized water for injection to things as relatively complicated as microspheres and biodegradable implants.

As medicaments, the compounds are preferably administered subcutaneously, topically, intranasally, intravenously, intramuscularly or locally (e.g. via an implant). Depot administration is also possible. However certain of the compounds (e.g. that described in EXAMPLE VII.d.) may be administered via an oral dosage form.

The exact dose and regimen for administration of these compounds and compositions will necessarily be dependent upon the needs of the individual subject to whom the medicament is being administered, the degree of affliction or need, and of course, the judgment of the medical practitioner. In general parenteral administration requires lower dosages than other methods of administration which are more dependent upon absorption. Illustratively however, the dosages are in the range of 0.01 to 10 mg per kilogram body mass.

The medicament manufactured with the compounds may also be used as adjuvant in acute anticoagulant therapy. In such a case, the medicament is administered with other compounds useful in treating such disease states.

The compounds may also be used with implantable pharmaceutical devices such as those described in U.S. Pat. No. 4,767,628, the contents of which are incorporated by this reference. Then the device will contain sufficient amounts of compound to slowly release the compound (e.g. for more than a month).

Methods of making medicaments which can be adapted to contain the compound for parenteral administration are described in the standard reference, Chase et al., *Remington's Pharmaceutical Sciences*, (16th ed., Mack Publishing Co., Easton. Pa., U.S.A., 1980) at pages 1463 through 1497.

The invention is further explained by reference to the following illustrative EXAMPLES.

EXAMPLES

If no configuration of the amino acid has been stated, the L form is intended.

I. The following abbreviations have been used for the various groups employed:

| tBu | = tertiary butyl |
|---|---|
| Me | = methyl |
| Z | = benzyloxycarbonyl |

II. The following abbreviations have been assigned to the solvents or reagents used:

| THF | = tetrahydrofuran |
|---|---|
| DCM | = dichloromethane |
| MeOH | = methanol |
| EA | = ethylacetate |
| OtBu | = tertiary butoxy |
| Mtr | = 4-methoxy-1,2,5-trimethylbenzenesulfonyl |
| Tol | = toluene |
| EtOH | = ethanol |
| Bu | = butanol |
| HOAc | = acetic acid |
| DMF | = N,N-dimethylformamide |
| DCC | = dicyclohexylcarbodiimide |
| DCU | = dicyclohexylurea |
| TFA | = trifluoro-acetic acid |
| N.E.M. | = N-ethylmoropholine |
| HOBt | = 1-hydroxybenztriazole |

III. The following abbreviations have been used throughout this specification of the amino-acid groups:

| Phe | = phenylalanyl |
|---|---|
| Pro | = prolyl |
| Arg | = arginyl |
| Asp | = aspartyl |
| Glu | = glutamyl |

-continued

| | |
|---|---|
| Gly | = glycyl |
| His | = histidyl |
| Lys | = lysyl |
| Tyr | = tyrosyl |
| Ile | = isoleucyl |
| Nle | = norleucyl |
| Cha | = cyclohexylalanyl |
| Val | = valyl |
| Leu | = leucyl |
| Ala | = alanyl |
| Aib | = aminoisobutyric acid |
| D-DPA | = diphenylalanyl |
| Har | = homoarginyl |
| Hly | = homolysine |
| Pec | = pipecolic acid |
| Nal(1) | = napthylalanyl (1) |
| Nal(2) | = napthylalanyl (2) |
| pClPhe | = p-chlorophenylalanyl |
| HPhe | = homo-phenylalanyl |

IV. All sequences mentioned herein are written according to the generally accepted convention wherein the N-terminal amino acid is on the left and the C-terminal amino acid is on the right, Example I 1.1 Z-D-Phe-Pro-Arg-Gly-Phe-OMe (SEQ ID NO:1)

A solution of the partially protected peptide Z-D-Phe-Pro-Arg-OH 0.5 g. (0.9 mmol) in 5 ml of DMF is cooled to 0° C. and 220 mg (1.6 mmol) of 1-hydroxybenzotriazole and 185 mg (0.9 mmol) of dicyclohexylcarbodiimide are added successively with stirring. The reaction mixture is stirred for 30 minutes; then a solution of H-Gly-Phe-OMe-HCl in 5 ml of DMF with sufficient triethylamine to give a pH of 7 is added. The mixture is stirred for 16 hours at room temperature. Thereafter, the dicyclohexylurea formed is removed by filtration. After evaporation of the filtrate, the residue is dissolved in water and extracted with $CH_2Cl_2$, the crude product is purified on $SiO_2$ with EA/pyridine/HOAc/$H_2O$ 6:1.5:1.5:1 (by vol.).

1.2 Z-D-Phe-Pro-Arg-Gly-Phe-OH (SEQ ID NO:1)

The methylester of 1.1 (0.2 g=0.25 mmol) is removed by treatment in dioxane and water at room temperature with sufficient 1N NaOH solution to give a pH of 13 for 1 hr. After acidification, the mixture is evaporated and extracted with methylene chloride to give 180 mg of the corresponding free acid.

1.3 H-D-Phe-Pro-Arg-Gly-Phe-OH (SEQ ID NO:1)

Hydrogenolysis of the partially protected pentapeptide (180 mg=0.24 mmol) using 18 mg of Pd/C 10% as the catalyst in methanol with 2 equivalents of 1N HCl gives the free title compound.

The material thus obtained was treated with an ion-exchange resin in the acetate form (Dowex) to convert the pentapeptide into the acetate salt. After removing the resin by filtration, the filtrate was lyophilized and the product purified by chromatography on $SiO_2$ with EA/pyridine/HOAc/$H_2O$ (6:2:2:1, by vol.) eluent. The pooled fractions were evaporated and lyophilized to give 80 mg of analytically pure product. Spectral data was in agreement with the assigned structure. Rf in EA/pyridine/HOAc/$H_2O$ 6:2:2:1= 0.44 (on $SiO_2$).

Example II 2.1 Z-Arg-Ala-OMe

The synthesis of 2.1 was carried out according to the method of Kraniova Bt. et al (*Zh Obskch Khim*, 30, 92 (1969).

2.2 Z-Arg-Ala-Phe-OtBu

Z-Arg-Ala-OMe was saponified using the prescription for compound 1.3. The free acid was coupled with H-Phe-OtBu using the same procedure described in EXAMPLE 1.2.

2.3 Boc-D-Phe-Pro-Arg-Ala-Phe-OtBu (SEQ ID NO:2)

A solution of 0.72 g (1.99 mmol) Boc-D-Phe-Pro-OH in 16 ml of DMF is cooled to 0° C. and 540 mg (3.99 mmol) of 1-hydroxy benzotriazole and 460 mg (2.2 mmol) of dicyclohexylcarbodiimide are added. The reaction mixture is stirred for 30 minutes. Then a solution of H-Arg-Ala-Phe-OtBu (obtained by catalytic hydrogenolysis of Z-Arg-Ala-Phe-OtBu in 16 ml of DMF with 2 eq. of 1N HCl) in 16 ml of DMF with sufficient N.E.M. to give a pH of 7 is added. The mixture is stirred for 16 hours at room temperature. The dicyclohexylurea formed is filtered off and the filtrate concentrated by evaporation. The residue is dissolved in $CH_2Cl_2$ and washed with 5% $NaHCO_3$ solution, 5% $KHSO_4$ solution and water. The organic phase is dried over anhydrous $Na_2SO_4$ and evaporated.

2.4 H-D-Phe-Pro-Arg-Ala-Phe-OH (SEQ ID NO:2)

The protecting groups of the pentapeptide of 2.3 are removed by treatment with 15 ml of 90% TFA in the presence of 0.6 ml of anisole. The mixture is stirred for 1 hour at room temperature. The material thus obtained is dissolved in t-BuOH/water (1:1, v/v) and treated with an ion-exchange resin in the acetate form. After filtering the resin, the filtrate is lyophilized and the product purified by chromatography on silica with a Bu/pyridine/HOAc/$H_2O$ (16:3:4:1, by vol.) eluent. The fractions containing the desired material are evaporated and then lyophilized to give 510 mg of the titled compound. Spectral data was in agreement with the assigned structure. Rf in Bu/pyridine/HOAc/$H_2O$ 8:3:1:4=0.45 (on $SiO_2$).

2.5 Boc-D-Phe-Pro-Arg Ala-Phe-Lys(Boc)OtBu. (SEQ ID NO:3)

Using the prescription for compound 2.3, 0.8 mmol of Boc-D-Phe-Pro-OH was coupled with 0.65 g (0.8 mmol) of Z-Arg-Ala-Phe-Lys(Boc)-OtBu.

2.6 H-D-Phe-Pro-Arg-Ala-Phe-Lys-OH. (SEQ ID NO:3)

The protecting groups of the pentapeptide 2.5 are removed using the prescription for compound 2.4. The analytically pure compound (0.1 g) was obtained, the spectral data of which agreed with the assigned structure. Rf in Bu/pyridine/HOAc/$H_2O$ (8:3:1:4)=0.3 (on $SiO_2$).

Example III

H-D-Phe-Pro-Arg-Gly-Phe-Lys-OH (SEQ ID NO:20) was prepared using a prescription analogous to that for compound 2.6. Analytical results agreed with the assigned structure. Rf in Bu/pyridine/HOAc/$H_2O$ 4:1:1:2=0.4 (on $SiO_2$).

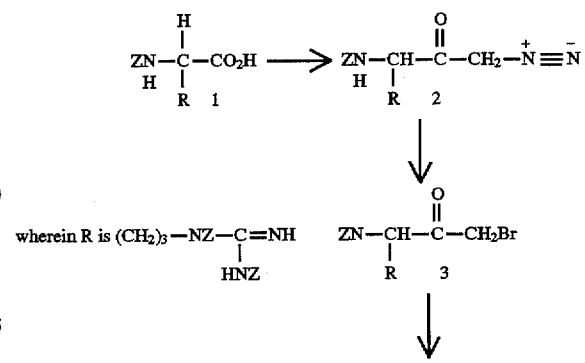

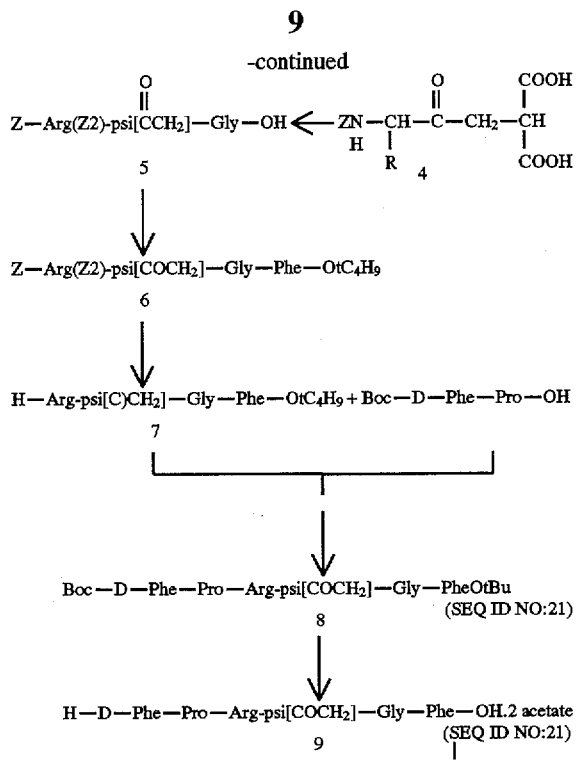

4.1 Z-Arg(Z$_2$)—CH$_2$Br

Nα, Nδ, NΩ-tri benzyloxycarbonyl-L-Arg was obtained from Nα-benzyloxycarbonyl-L-Arg by the method of W üdnsch and Wendlberger (*Chem. Ber.*, 100, p. 160 (1967)) in 30% yield. Rf on SiO$_2$ is 0.43 in toluene/EtOH (8:2).

Compound 1 (36.0 mmol) was dissolved in dry THF and the mixed anhydride was prepared with isobutylchloroformate and N.E.M. An ethereal solution of diazomethane was added in several portions, and after stirring for 20 hours, the diazomethylketone 2 was formed. Rf is 0.67 (Tol/EtOH, 8:2) on SiO$_2$.

The reaction mixture was cooled to 0° C. and an ethereal solution of HBr was added and the reaction was followed by TLC. After extraction with water and ether, compound 3 could be obtained in crystal form. Rf on SiO$_2$ is 0.81 (Tol/EtOH, 8:2).

4.2 Z-Arg (Z$_2$)-psi[CO-CH$_2$]Gly-OH (5)

To a solution of compound 3 in dry THF (17.54 mmol in 75 ml) a solution of the sodium salt of di(t-butyldimethylsilyl malonate in THF was added dropwise with stirring. The coupling was complete after 3 hours at room temperature. In situ acidic removal of the ester groups followed by extraction with CH$_2$Cl$_2$ and subsequent evaporation gave compound 4 as a yellow oil. Rf on SiO$_2$ is 0.51 (CH$_2$Cl$_2$/MeOH, 8/2).

Decarboxylation of compound 4 was carried out by refluxing in toluene for 1 hour. After chromatography, the pure ketomethylene isosteric dipeptide 5 was obtained as a white amorphous powder. Rf on SiO$_2$ is 0.17 (CH$_2$Cl$_2$/MeOH, 9/1).

4.3 H-Arg-psi[CO—CH$_2$]-Gly-PheOtBu (7)

HOBt was added (0.58 mmol, 79.1 mg) to a solution of 5 (0.39 mmol, 0.25 g) in DMF (1.0 ml). The solution was cooled to 0° C. and DCC (0.43 mmol, 88.7 mg) was added. After 1 hour of stirring, a solution of H-Phe-OtBu-HCl (0.59 mmol, 0.21 g) in DMF, adjusted to pH 7.5 with N.E.M., was added. The mixture was then stirred until no starting compound 5 wa detectable via TLC. The reaction mixture was cooled to −20° C. and the precipitated DCU filtered off. The filtrate was concentrated and the residue dissolved in CH$_2$Cl$_2$. The organic layer was washed in Na$_2$CO$_3$ and KHSO$_4$ solution. After washing with water, the organic layer was dried over Na$_2$SO$_4$. Filtration and evaporation yielded 6 in 92%. Rf(6)=0.60 (Tol/EtOH 8/2).

Crude product 6 (119 mg, 0.14 mmol) was dissolved in DMF, and after adding 50 mg Pd/C (10%), H$_2$ was bubbled through the mixture until no starting compound was left. Two equivalents of HCl were added (0.28 ml, 2N HCl). Compound 7 was obtained quantitatively, after filtering off the catalyst and concentrating the filtrate. Rf (7) is 0.33 in EA/pyridine/HOAc/H$_2$O (6/2/2/1).

4.4 H-D-Phe-Pro-Arg-psi[COCH$_2$]-Gly-Phe-OH (9) (SEQ ID NO:21)

Boc-D-Phe-Pro-OH was dissolved in DMF (0.20 mmol, 72.7 mg) and coupled to 7 (0.14 mmol, 89.6 mg) via a HOBt (0.3mmol, 40 mg)/DCC (0.22 mmol, 41.4 mg) mediated coupling as described for compound 6. Compound 8 was obtained. Rf=0.27 in EA/pyridine/HOAc/H$_2$O (80/20/6/5).

To the crude product 8 (135 mg), 90% TFA was added (5 ml) and anisole as a scavenger. After 1 hour, the reaction was complete, and the mixture was poured into ether. The resulting precipitate was filtered off, washed with ether, and dissolved in water/t-butanol (1/1). Dowex Ac was added to exchange the TFA anion with acetate anions. The ion exchanger was removed by filtration and the product 9 was freeze-dried. The product was purified by column chromatography Bu/pyridine/HOAc/H$_2$O (4/0.75/0.25/1). Rf(9)= 0.19.

Examples V & VI

H-D-Phe-Pro-Arg-Gly-His-OH (SEQ ID NO:4) and H-D-Phe-Pro-Arg-psi[COCH$_2$]-Gly-Phe-Lys-OH (SEQ ID NO:22) were prepared in manners similar to EXAMPLE I and EXAMPLE IV respectively.

Example VII

In a similar manner the following diketo isosteres are prepared:
a) H-D-Phe-Pro-Arg-CO-Phe-OH;
b) H-D-Phe-Pro-Arg-CO-Phe-Lys-OH;
c) H-D-Phe-Pro-Arg-CO-Gly-Phe-Lys-OH; and
d) H-D-Phe-Pro-Arg-CO-D-Phe-D-Tyr-OH.

Example VIII

Synthesis of

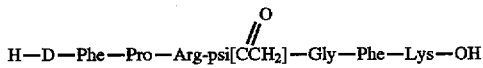

(SEQ ID NO:22)

a. Compound 5 of EXAMPLE 4.2 (1.00 g, 1.58 mmol) was activated with HOBt (0.32 g, 2.39 mmol) and DCC (0.36 g, 1.74 mmol) in DMF (10 ml @ 0° C.). A solution of H-Phe-Lys(Boc)OtBu (2.49 mmol) in DMF (10 ml) was adjusted to pH 7.5 with NEM and added to the activated compound 5, which had been stirred for 1 hour at room temperature. The mixture was stirred until no compound 5 could be detected on TLC. The reaction mixture was worked up in the same manner as compound 6 in EXAMPLE 4.3, to obtain compound 10 (i.e. Z-Arg(Z)$_2$-psi[CO—CH$_2$]-Gly-phe-Lys(Boc)OtBu) in 85%. Rf(compound 10)=0.29 (DMC/ EA. 8/2).

b. The crude product 10 was dissolved in DMF (0.47 mmol, 0.5 g in 10 ml). After adding Pd/C (50 mg) H$_2$ was bubbled through the solution until no starting compound was detectable on TLC. Two equivalents of HCl were added before removing the catalyst by filtration. Compound 11 (i.e.

H-Arg psi[CO—CH₂]-Gly-Phe-Lys(Boc)OtBu was kept in solution and immediately used in the synthesis of compound 12. Rf(compound 11)=0.43 (EA/pyridine/HOAc/water, 6/2/2/1).

c. Boc-D-Phe-Pro-OH was dissolved in DMF (0.705 mmol, 256 mg) cooled to 0° C. and HOBt (1.05 mmol, 143 mg) and DCC (0.78 mmol, 160 mg) were added. The same procedure was followed as described in this EXAMPLE VIII.a., above, to give compound 12, i.e.:

(SEQ ID NO:22) Rf(compound 12)=0.27 in (EA/Pyridine/HOAc/water 6/2/2/1).

d. Compound 12 was then dissolved in 90% TFA (2.5 ml) and anisole was added as a scavenger. After 1 hour, the mixture was worked up as described in EXAMPLE 4.4 to give compound 13, i.e. the titled compound (H-D-Phe-Pro-Arg-psi[COCH₂]-Gly-Phe-Lys-OH) (SEQ ID NO:22), finally as an acetate salt. Compound 13 was freeze-dried and purified by column chromatography. Rf(compound 13)= 0.12 (EA/pyridine/HOAc/water 6/2/2/1). Compound 13 is a highly potent, highly potent, highly selective Factor IIa inhibitor.

Example IX

The following compounds were prepared, and all had Factor IIa binding activity:
a. H-D-Nle-Pro-Arg-Ala-Phe-Lys-OH; (SEQ ID NO:5)
b. H-D-Phe-Val-Arg-Ala-Phe-Lys-OH; (SEQ ID NO:6)
c. H-D-Phe-Pro-Arg-Ser-Phe-Lys-OH; (SEQ ID NO:7)
d. H-D-Phe-Pro-Arg-Ala-Cha-Lys-OH; (SEQ ID NO:8)
e. H-D-Phe-Pro-Arg-Ala-Nal(1)-Lys-OH; (SEQ ID NO:9)
f. H-D-Phe-Pro-Arg-Ala-Nal(2)-Lys-OH; (SEQ ID NO:10)
g. H-D-Phe-Pro-Arg-Ala-pClPhe-Lys-OH; (SEQ ID NO:11)
h. H-D-Phe-Pro-Arg-Ala-D-αMeTyr-Lys-OH; (SEQ ID NO:12)
i. H-D-Phe-Pro-Arg-Ala-L-αMeTyr-Lys-OH; (SEQ ID NO:13)
j. H-D-Phe-Pro-Arg-Ala-HPhe-Lys-OH; (SEQ ID NO:14)
k. H-D-Phe-Pro-Arg-Ala-Phe-Pec-OH; (SEQ ID NO:15) and
l. H-D-Phe-Pro-Arg-Ala-Phe-Arg-OH (SEQ ID NO:16).

Example X

The following compounds are prepared in a similar manner:
a. H-D-Phe-Pro-Arg-Ala-αMePhe-Lys-OH (SEQ ID NO:17),
b. H-D-Ile-Val-p-AmPhe-Ala-Cha-Arg-OH (SEQ ID NO:18), and
c. H-D-Phe-Pro-Arg-psi[COCH₂]-Ala-Nal (2) -Lys-OH (SEQ ID NO:23).

Example XI

FACTOR IIa INHIBITORY ACTIVITY

The inhibition of human thrombin was investigated by continuously monitoring the splitting of the chromogenic substance S 2238 (N-D-Phe-L-pipecolyl-L-Arg-p-nitroanilide 2 HCl) in the absence and in the presence of 3, 1, 0.3, 0.1 and 0.03 mM of the compound investigated. These measurements were performed with the help of a kinetic microtiter plate reader. From these measurements the end absorbances were calculated after 90 minutes. Based on these total scores, an $IC_{50}$ of the various compounds investigated is expressed as the molar concentration which inhibited the end absorbance by 50%. $IC_{50}$ values for aXa-activity were investigated in the same way by using the chromogenic substrate s2222 (N-benzoyl-Ile-Glu-(OCH₃)Gly-Arg-pNa).

IC 50 values measured after 90 minutes and the ratio aIIa over aXa.

| COMPOUND | $IC_{50}$ aIIa | $IC_{50}$ aXa | $IC_{50}$ aIIa: aXa |
|---|---|---|---|
| H-D-Phe-Pro-Arg-Gly-OH (SEQ ID NO:19) | 4.0 E-3 | 4.8 E-3 | 1 |
| H-D-Phe-Pro-Arg-Gly-Phe-OH (SEQ ID NO:1) | 4.1 E-4 | 1.3 E-3 | 3 |
| H-D-Phe-Pro-Arg-Gly-Phe-Lys-OH (SEQ ID NO:20) | 2.5 E-4 | 1.6 E-3 | 6 |
| H-D-Phe-Pro-Arg-Ala-Phe-Lys-OH (SEQ ID NO:3) | 1.1 E-4 | 3.1 E-3 | 28 |
| H-D-Phe-Pro-Arg-psi[COCH₂]-Gly-Phe-OH (SEQ ID NO:2) | 3.7 E-5 | 2.1 E-3 | 57 |

Example XII

The following data shows minimum inhibitory concentrations ($K_i[M]$) of various compounds of the invention in comparison with a prior art compound (EXAMPLE XII.a), and the effect of incorporating an isosteric linkage into the peptides.

| COMPOUND | $K_i[M]$-Factor IIa |
|---|---|
| a. H-D-Phe-Pro-Arg-Gly-OH (SEQ ID NO:19) | $7.0 \times 10^{-5}$ |
| b. H-D-Phe-Pro-Arg-psi[COCH₂]-Gly-OH (SEQ ID NO:24) | $2.6 \times 10^{-5}$ |
| c. H-D-Phe-Pro-Arg-Gly-Phe-OH (SEQ ID NO:1) | $7.6 \times 10^{-6}$ |
| d. H-D-Phe-Pro-Arg-psi[COCH₂]-Gly-Phe-OH (SEQ ID NO:21) | $4.8 \times 10^{-7}$ |
| e. H-D-Phe-Pro-Arg-Gly-Phe-Lys-OH (SEQ ID NO:3) | $3.4 \times 10^{-6}$ |
| f. H-D-Phe-Pro-Arg-psi[COCH₂]-Gly-Phe-Lys-OH (SEQ ID NO:22) | $2.8 \times 10^{-8}$ |

References herein to specific Examples or embodiments should not be interpreted as limitations to the invention's scope which is determined by the claims.

What is claimed is:

1. A compound comprising the formula:

X Y Z A P Q T wherein X is H, $CH_3$, an acyl group or a general protective group;

Y is D-Phe or D-Nle;

Z is Pro;

A is selected from the group consisting of Arg-Gly, Arg-Ala, Arg-psi[CO—$CH_2$]-Gly, Arg-psi[CO—$CH_2$]-Ala, and Arg-CO-Gly;

P is selected from the group consisting of L/D-Phe, L/D-Lys, L/D-His, D-Tyr, L/D-Cha, L/D-Nal(1), L/D-Nal(2), L/D-pClPhe, L/D-αMeTyr, HPhe, Arg and αMePhe;

Q is a bond or an amino acid selected from the group consisting of Arg, Lys, Pec, and D-Tyr; and T is —OH, —$OR^4$, —$N(CH_2)_{1-6}NR^4R^5$ or N—$R^4R^5$, wherein $R^4$ and $R^5$ are independently selected from the group consisting of H, alkyl, aryl, aralkyl, or wherein $R^4$ and $R^5$ together with the nitrogen atom to which they are bonded to form a ring;

or a pharmaceutically acceptable salt thereof;

wherein said compound acts as a reversible thrombin inhibitor.

2. The compound of claim 1, wherein P is L-Phe.

3. The compound of claim 1, wherein Q is L-Lys or L-Arg.

4. The compound of claim 1, having the formula: H-D-Phe-pro-Arg-psi[COCH$_2$]-Gly-phe-Lys-OH.

5. A pharmaceutical composition comprising a pharmaceutical carrier and a pharmaceutically effective amount of a compound of claim 1.

6. A pharmaceutical composition comprising a pharmaceutical carrier and a pharmaceutically effective amount of the compound of claim 4.

* * * * *

SEQUENCE LISTING ( 1 ) GENERAL INFORMATION:

( i i i ) NUMBER OF SEQUENCES: 24

( 2 ) INFORMATION FOR SEQ ID NO: 1:

-continued (i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa1 is D-Phe."

(xi) SEQUENCE DESCRIPTION: SEQ ID NO: 1:

Xaa Pro Arg Gly Phe
1               5

(2) INFORMATION FOR SEQ ID NO: 2:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa1 is D-Phe."

(xi) SEQUENCE DESCRIPTION: SEQ ID NO: 2:

Xaa Pro Arg Ala Phe
1               5

(2) INFORMATION FOR SEQ ID NO: 3:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa1 is D-Phe."

(xi) SEQUENCE DESCRIPTION: SEQ ID NO: 3:

Xaa Pro Arg Ala Phe Lys
1               5

(2) INFORMATION FOR SEQ ID NO: 4:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa1 is D-Phe."

(xi) SEQUENCE DESCRIPTION: SEQ ID NO: 4:

Xaa Pro Arg Gly His
1               5

(2) INFORMATION FOR SEQ ID NO: 5:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa1 is D-Nle."

( x i ) SEQUENCE DESCRIPTION: SEQ ID NO: 5:

```
Xaa  Pro  Arg  Ala  Phe  Lys
 1                    5
```

( 2 ) INFORMATION FOR SEQ ID NO: 6:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa1 is D-Phe."

( x i ) SEQUENCE DESCRIPTION: SEQ ID NO: 6:

```
Xaa  Val  Arg  Ala  Phe  Lys
 1                    5
```

( 2 ) INFORMATION FOR SEQ ID NO: 7:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa1 is D-Phe."

( x i ) SEQUENCE DESCRIPTION: SEQ ID NO: 7:

```
Xaa  Pro  Arg  Ser  Phe  Lys
 1                    5
```

( 2 ) INFORMATION FOR SEQ ID NO: 8:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa1 is D-Phe."

( i x ) FEATURE:
    ( A ) NAME/KEY: Modified-site
    ( B ) LOCATION: 5
    ( D ) OTHER INFORMATION: /note= "Xaa5 is Cha
        (cyclohexylalanine)."

( x i ) SEQUENCE DESCRIPTION: SEQ ID NO: 8:

Xaa Pro Arg Ala Xaa Lys
1               5

(2) INFORMATION FOR SEQ ID NO: 9:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa1 is D-Phe."

(ix) FEATURE:
        (A) NAME/KEY: Modified-site
        (B) LOCATION: 5
        (D) OTHER INFORMATION: /note= "Xaa5 is Nal(1) (1-naphthylalanine)."

(xi) SEQUENCE DESCRIPTION: SEQ ID NO: 9:

Xaa Pro Arg Ala Xaa Lys
1               5

(2) INFORMATION FOR SEQ ID NO: 10:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa1 is D-Phe."

(ix) FEATURE:
        (A) NAME/KEY: Modified-site
        (B) LOCATION: 5
        (D) OTHER INFORMATION: /note= "Xaa5 is Nal(2) (2-naphthylalanine)."

(xi) SEQUENCE DESCRIPTION: SEQ ID NO: 10:

Xaa Pro Arg Ala Xaa Lys
1               5

(2) INFORMATION FOR SEQ ID NO: 11:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa1 is D-Phe."

(ix) FEATURE:
        (A) NAME/KEY: Modified-site
        (B) LOCATION: 5
        (D) OTHER INFORMATION: /note= "Xaa5 is pClPhe (p-chlorophenylalanine)."

(xi) SEQUENCE DESCRIPTION: SEQ ID NO: 11:

Xaa Pro Arg Ala Xaa Lys (2) INFORMATION FOR SEQ ID NO: 12:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa1 is D-Phe."

(ix) FEATURE:
        (A) NAME/KEY: Modified-site
        (B) LOCATION: 5
        (D) OTHER INFORMATION: /note= "Xaa5 is D-alphaMeTyr (alpha methyltyrosine)."

(xi) SEQUENCE DESCRIPTION: SEQ ID NO: 12:

```
Xaa  Pro  Arg  Ala  Xaa  Lys
1                    5
```

(2) INFORMATION FOR SEQ ID NO: 13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa1 is D-Phe."

(ix) FEATURE:
        (A) NAME/KEY: Modified-site
        (B) LOCATION: 5
        (D) OTHER INFORMATION: /note= "Xaa5 is L-alphaMeTyr (alpha methyltyrosine)."

(xi) SEQUENCE DESCRIPTION: SEQ ID NO: 13:

```
Xaa  Pro  Arg  Ala  Xaa  Lys
1                    5
```

(2) INFORMATION FOR SEQ ID NO: 14:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa1 is D-Phe."

(ix) FEATURE:
        (A) NAME/KEY: Modified-site
        (B) LOCATION: 5
        (D) OTHER INFORMATION: /note= "Xaa5 is HPhe (homophenylalanine)."

(xi) SEQUENCE DESCRIPTION: SEQ ID NO: 14:

```
Xaa  Pro  Arg  Ala  Xaa  Lys
1                    5
```

( 2 ) INFORMATION FOR SEQ ID NO: 15:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa1 is D-Phe."

( i x ) FEATURE:
        ( A ) NAME/KEY: Modified-site
        ( B ) LOCATION: 6
        ( D ) OTHER INFORMATION: /note= "Xaa6 is Pec (pipecolic acid)."

( x i ) SEQUENCE DESCRIPTION: SEQ ID NO: 15:

Xaa Pro Arg Ala Phe Xaa
    1               5

( 2 ) INFORMATION FOR SEQ ID NO: 16:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa1 is D-Phe."

( x i ) SEQUENCE DESCRIPTION: SEQ ID NO: 16:

Xaa Pro Arg Ala Phe Arg
    1               5

( 2 ) INFORMATION FOR SEQ ID NO: 17:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa1 is D-Phe."

( i x ) FEATURE:
        ( A ) NAME/KEY: Modified-site
        ( B ) LOCATION: 5
        ( D ) OTHER INFORMATION: /note= "Xaa5 is alphaMePhe (alpha methylphenylalanine)."

( x i ) SEQUENCE DESCRIPTION: SEQ ID NO: 17:

Xaa Pro Arg Ala Xaa Lys
    1               5

( 2 ) INFORMATION FOR SEQ ID NO: 18:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa1 is D-Ile."

( i x ) FEATURE:
    ( A ) NAME/KEY: Modified-site
    ( B ) LOCATION: 3
    ( D ) OTHER INFORMATION: /note= "Xaa3 is p-AmPhe (p-aminophenylalanine)."

( i x ) FEATURE:
    ( A ) NAME/KEY: Modified-site
    ( B ) LOCATION: 5
    ( D ) OTHER INFORMATION: /note= "Xaa5 is Cha (cyclohexylalanine)."

( x i ) SEQUENCE DESCRIPTION: SEQ ID NO: 18:

```
Xaa  Val  Xaa  Ala  Xaa  Arg
 1                     5
```

( 2 ) INFORMATION FOR SEQ ID NO: 19:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa1 is D-Phe."

( x i ) SEQUENCE DESCRIPTION: SEQ ID NO: 19:

```
Xaa  Pro  Arg  Gly
 1
```

( 2 ) INFORMATION FOR SEQ ID NO: 20:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa1 is D-Phe."

( x i ) SEQUENCE DESCRIPTION: SEQ ID NO: 20:

```
Xaa  Pro  Arg  Gly  Phe  Lys
 1                     5
```

( 2 ) INFORMATION FOR SEQ ID NO: 21:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note= "Xaa1 is D-Phe."

( i x ) FEATURE:

(A) NAME/KEY: Modified-site
(B) LOCATION: 3..4
(D) OTHER INFORMATION: /note= "Xaa3-Xaa4 is Arg-psi[COCH2]-Gly."

(xi) SEQUENCE DESCRIPTION: SEQ ID NO: 21:

Xaa Pro Xaa Xaa Gly Phe
1               5

(2) INFORMATION FOR SEQ ID NO: 22:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa1 is D-Phe."

(ix) FEATURE:
(A) NAME/KEY: Modified-site
(B) LOCATION: 3..4
(D) OTHER INFORMATION: /note= "Xaa3-Xaa4 is Arg-psi[COCH2]-Gly."

(xi) SEQUENCE DESCRIPTION: SEQ ID NO: 22:

Xaa Pro Xaa Xaa Phe Lys
1               5

(2) INFORMATION FOR SEQ ID NO: 23:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa1 is D-Phe."

(ix) FEATURE:
(A) NAME/KEY: Modified-site
(B) LOCATION: 3..4
(D) OTHER INFORMATION: /note= "Xaa3-Xaa4 is Arg-psi[COCH2]-Ala."

(ix) FEATURE:
(A) NAME/KEY: Modified-site
(B) LOCATION: 6
(D) OTHER INFORMATION: /note= "Xaa6 is Nal(2) (2-naphthylalanine)."

(xi) SEQUENCE DESCRIPTION: SEQ ID NO: 23:

Xaa Pro Xaa Xaa Ala Xaa Lys
1               5

(2) INFORMATION FOR SEQ ID NO: 24:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:

```
        ( A ) NAME/KEY: Modified-site
        ( B ) LOCATION: 1
        ( D ) OTHER INFORMATION: /note= "Xaa1 is D-Phe."

( i x ) FEATURE:
        ( A ) NAME/KEY: Modified-site
        ( B ) LOCATION: 3..4
        ( D ) OTHER INFORMATION: /note= "Xaa3-Xaa4 is
                Arg-psi[COCH2]-Gly."

( x i ) SEQUENCE DESCRIPTION: SEQ ID NO: 24:

Xaa  Pro  Xaa  Xaa
    1
```